United States Patent
Kawai

(10) Patent No.: US 7,038,189 B2
(45) Date of Patent: May 2, 2006

(54) OPTOELECTRONIC DUST SENSOR AND AIR CONDITIONING EQUIPMENT IN WHICH SUCH OPTOELECTRONIC DUST SENSOR IS INSTALLED

(75) Inventor: Noboru Kawai, Nabari (JP)

(73) Assignee: Sharp Kabushiki Kaisha, Osaka (JP)

( * ) Notice: Subject to any disclaimer, the term of this patent is extended or adjusted under 35 U.S.C. 154(b) by 129 days.

(21) Appl. No.: 10/801,005

(22) Filed: Mar. 16, 2004

(65) Prior Publication Data

US 2004/0188598 A1    Sep. 30, 2004

(30) Foreign Application Priority Data

Mar. 25, 2003  (JP)  ............... 2003-082912

(51) Int. Cl.
  *G01V 8/00*  (2006.01)
  *H01J 40/14*  (2006.01)
(52) U.S. Cl. ................... 250/222.2; 340/630
(58) Field of Classification Search ............ None
See application file for complete search history.

(56) References Cited

U.S. PATENT DOCUMENTS 4,906,978 A * 3/1990 Best et al. ............ 340/630
5,319,827 A * 6/1994 Yang ..................... 15/319
2004/0155178 A1* 8/2004 Ito ..................... 250/231.13

FOREIGN PATENT DOCUMENTS

JP     8-62136    3/1996

* cited by examiner

*Primary Examiner*—Stephone B. Allen
*Assistant Examiner*—Suezu Ellis
(74) *Attorney, Agent, or Firm*—Nixon & Vanderhye P.C.

(57) ABSTRACT

At an optoelectronic dust sensor, opening(s) is/are formed at front panel(s) of main body housing(s), and passage hole(s) is/are formed at back panel(s) of main body housing(s). Provided between such back panel passage hole(s) and front panel opening(s) is/are dust passage route(s) permitting passage of dust and/or smoke. Passage hole(s) is/are for introducing dust and/or smoke to dust passage route(s). Opening(s), being for discharging dust and/or smoke from dust passage route(s), is/are sufficiently larger than passage hole(s).

6 Claims, 4 Drawing Sheets

OPTOELECTRONIC DUST SENSOR AND AIR CONDITIONING EQUIPMENT IN WHICH SUCH OPTOELECTRONIC DUST SENSOR IS INSTALLED

BACKGROUND OF INVENTION

This application claims priority under 35 USC 119(a) to Patent Application No. 2003-082912 filed in Japan on 25 Mar. 2003, the content of which is incorporated herein by reference in its entirety.

The present invention pertains to an optoelectronic dust sensor detecting presence, absence, and/or concentration of dust and/or smoke floating within room(s), and to air conditioning equipment in which such optoelectronic dust sensor(s) is/are installed.

Optoelectronic dust sensors of this type may be provided, for example, at air filters, air scrubbers, air coolers, and other such air conditioning equipment, where they are used to detect presence, absence, and/or concentration of dust and/or smoke contained within air circulated by air conditioning equipment.

FIG. 6(a), FIG. 6(b), FIG. 6(c), and FIG. 6(d) are a sectional view, front view, bottom view, and rear view showing a conventional optoelectronic dust sensor (see Japanese Patent Application Publication Kokai No. H8-62136 (1996). At this sensor, dust passage holes 102a, 103a are respectively formed at front panel 102 and back panel 103 of main body housing 101; dust being introduced from dust passage hole 103a at the back thereof, the dust being made to pass through a dust passage route between respective dust passage holes 102a, 103a, and the dust being discharged from dust passage hole 102a at the front thereof. Light-emitting unit 104 is equipped with light-emitting element 104a, lens 104b, and slit 104c; light from light-emitting element 104a being collimated by lens 104b and thereafter being incident on the dust passage route. Light-receiving unit 105 is equipped with light-receiving element 105a, lens 105b, and slit 105c; light from the dust passage route being condensed onto light-receiving element 105a by Here, in the event that there is no dust or smoke passing through the dust passage route, because almost all of the light from light-emitting unit 104 will pass through the dust passage route and reach optical isolation region 106, the amount of light received at light-receiving unit 105 will be extremely small. Furthermore, in the event that there is dust and/or smoke passing through the dust passage route, because a portion of the light from light-emitting unit 104 will be reflected by the dust and/or smoke in the dust passage route and will be incident on light-receiving unit 105, the amount of light received at light-receiving unit 105 will increase. Accordingly, presence and/or absence of dust and/or smoke passing through the dust passage route may be detected based on variation in received-light output at light-receiving element 105a of light-receiving unit 105; and/or concentration of dust and/or smoke passing through the dust passage route may be detected based on the received-light output level at light-receiving element 105a.

However, with the foregoing conventional optoelectronic dust sensor, because the dust passage route is provided within main body housing 101, dust and/or smoke being made to pass through the dust passage route, there is a tendency for dust and/or smoke to accumulate within main body housing 101 and for deposits to collect therein. In the event that the amount of deposits collected within this main body housing 101 becomes too large, it will sometimes be the case that a portion of the light from light-emitting unit 104 is reflected in diffuse fashion by the deposits which have collected within main body housing 101 and is incident on light-receiving unit 105, this then causing an increase in the amount of light received at light-receiving unit 105 and contributing to mistaken detection of dust and/or smoke.

And yet, at the foregoing conventional optoelectronic sensor, there having been no consideration made with respect to removal of deposits that have collected within main body housing 101, removal of deposits has been difficult; a vacuum cleaner or the like being employed in practice to suck away deposits by way of the small respective dust passage holes 102a, 103a.

The present invention was therefore conceived in light of the foregoing conventional problems, it being an object thereof to provide an optoelectronic dust sensor permitting easy removal of deposits that have collected within the main body housing thereof, and air conditioning equipment in which such optoelectronic dust sensor(s) is/are installed.

SUMMARY OF INVENTION

In order to solve the foregoing and/or other problems, an optoelectronic dust sensor in accordance with one or more embodiments of the present invention may comprise one or more light-emitting units irradiating one or more dust passage routes with light; one or more light-receiving units receiving light reflected from dust passing through at least one of the dust passage route or routes; one or more main body housings at least partially enclosing the optoelectronic dust sensor; one or more passage holes, provided at at least one of the main body housing or housings, for permitting introduction of dust from the exterior to at least one of the dust passage route or routes; and one or more openings, provided at at least one of the main body housing or housings, for permitting discharge of dust from at least one of the dust passage route or routes to the exterior; wherein presence, absence, and/or concentration of dust is detected based on received-light output from at least one of the light-receiving unit or units; and at least one of the opening or openings is larger than at least one of the passage hole or holes.

In accordance with embodiment(s) of the present invention constituted in such fashion, passage hole(s) and opening(s) may be formed on main body housing(s) of optoelectronic dust sensor(s), dust passage route(s) may be provided between passage hole(s) and opening(s), and opening(s) may be larger than passage hole(s). Wide opening(s) provided at side(s) from which dust is discharged may facilitate discharge of dust. Furthermore, dust may be less likely to collect within main body housing(s). Furthermore, it may be the case that deposits within main body housing(s) can be easily removed by way of large opening(s). In addition, when one or more optoelectronic dust sensors as described above is or are, for example, disposed near one or more air inlets of air conditioning equipment, at least one of the opening or openings of at least one of the optoelectronic sensor or sensors may be directed toward the inside of the air conditioning equipment, and at least one of the passage hole or holes of at least one of the optoelectronic sensor or sensors may be directed toward the outside of the air conditioning equipment. That is, by arranging main body housing(s) of optoelectronic dust sensor(s) such that small passage hole(s) is/are directed toward bright side(s) and large opening(s) is/are directed toward dark side(s), it is possible to reduce level(s) of exterior light incident at main body housing(s) by way of small passage hole(s), reducing likelihood of occurrence of mistaken detection of dust at light-receiving unit(s).

Furthermore, in one or more embodiments of the present invention, at least one of the opening or openings may be provided with at least one removably installed cover.

Such cover(s) may be provided at opening(s), and cover(s) may be actuated to uncover opening(s) when detecting dust.

Moreover, in one or more embodiments of the present invention, at least one of the cover or covers may be disposed so as to be removed by at least one distance from at least one optical path from at least one of the light-emitting unit or units, through dust in at least one of the dust passage route or routes, to at least one of the light-receiving unit or units.

As a result of disposing cover(s) in such fashion, light from light-emitting unit(s) may be reflected by cover(s) so as not to be incident on light-receiving unit(s), eliminating this as a factor in mistaken detection of dust at light-receiving unit(s).

Furthermore, one or more embodiments of the present invention may further comprise one or more detection report means for detecting and reporting one or more large amounts of dust accumulated at the interior of at least one of the main body housing or housings of the optoelectronic dust sensor.

Provision of such detection report means may make it easier to know when deposits should be removed.

DESCRIPTION OF PREFERRED EMBODIMENTS

Figure 1:
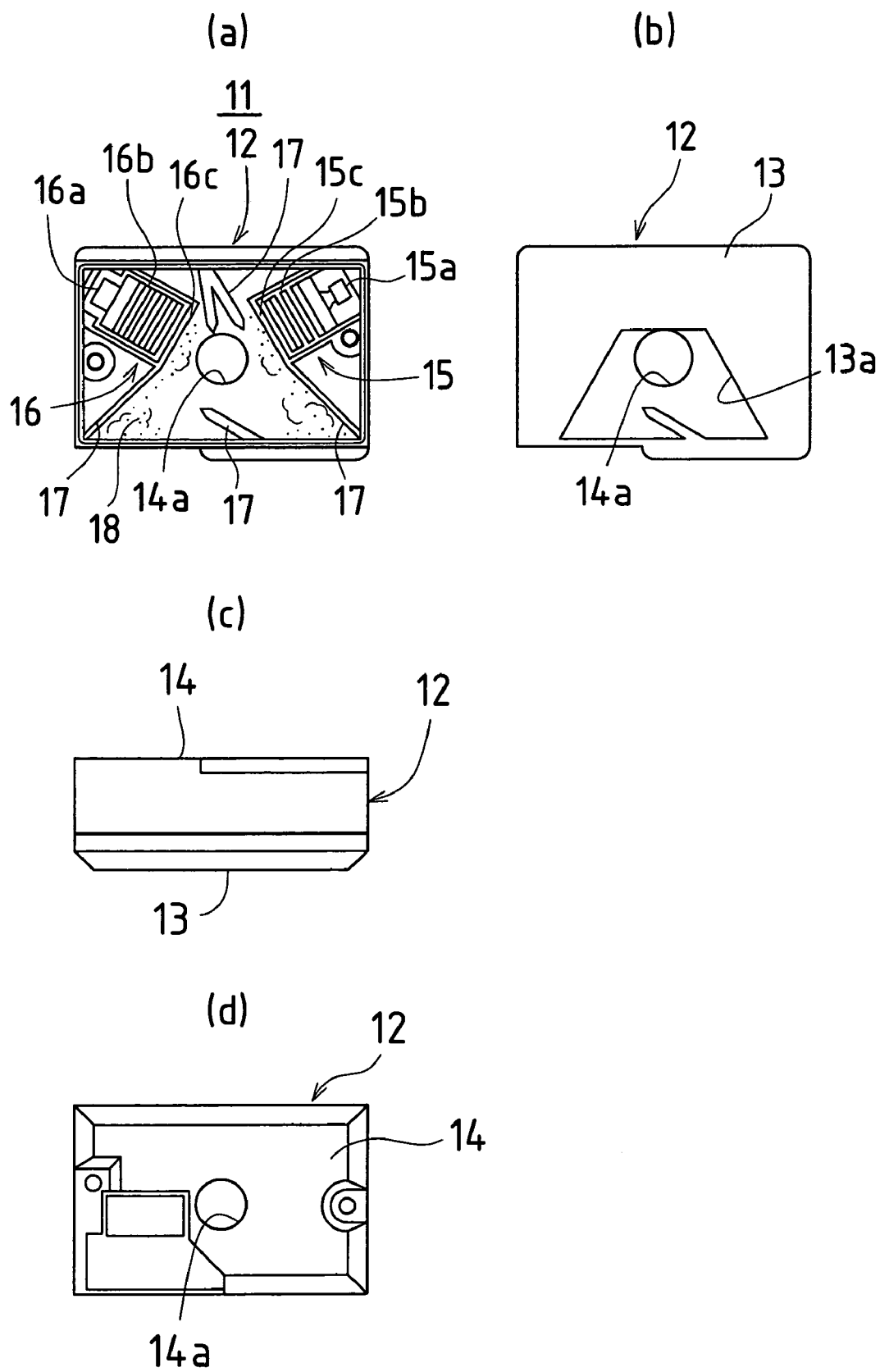
FIG. 1(a), FIG. 1(b), FIG. 1(c), and FIG. 1(d) are a sectional view, front view, bottom view, and rear view showing an embodiment of an optoelectronic dust sensor in accordance with the present invention.

Below, embodiments of the present invention are described in detail with reference to the attached drawings.

FIG. 1(a), FIG. 1(b), FIG. 1(c), and FIG. 1(d) are a sectional view, front view, bottom view, and rear view showing an embodiment of an optoelectronic dust sensor in accordance with the present invention.

At optoelectronic dust sensor 11 of the present embodiment, opening 13a is formed at front panel 13 of main body housing 12, and passage hole 14a is formed at back panel 14 of main body housing 12, a dust passage route permitting passage of dust and/or smoke being provided between passage hole 14a of back panel 14 and opening 13a of front panel 13. Passage hole 14a is for introducing dust and/or smoke to the dust passage route. Opening 13a, being for discharging dust and/or smoke from the dust passage route, is sufficiently larger than passage hole 14a.

Furthermore, light-emitting unit 15 and light-receiving unit 16 are respectively arranged so as to be directed toward the dust passage route. Plurality of optical baffles 17 are arranged in distributed fashion as appropriate, preventing light from light-emitting unit 15 from being directly incident on light-receiving unit 16 and forming optical isolation region(s) 18.

Light-emitting unit 15 is equipped with light-emitting element 15a, lens 15b, and slit 15c; light from light-emitting element 15a being collimated by lens 15b, the cross-section of the collimated light beam being narrowed and/or shaped by slit 15c, and this thereafter exiting therefrom such that it is directed at the dust passage route. Light-receiving unit 16 is equipped with light-receiving element 16a, lens 16b, and slit 16c; light from the dust passage route being condensed onto light-receiving element 16a by way of slit 16c and lens 16b.

Lens 15b and slit 15c of light-emitting unit 15 are for causing the light from light-emitting element 15a to be concentrated in which light from light-emitting element 15a could be dispersed and reflected within main body housing 12, causing unwanted light to be incident on light-receiving unit 16. Furthermore, lens 16b and slit 16c of light-receiving unit 16 are for causing only light which is reflected by dust and/or smoke in the dust passage route to be received at light-receiving element 16a, preventing situations in which unwanted light reflected within main body housing 12 is received at light-receiving element 16a.

At this optoelectronic dust sensor 11, in the event that there is no dust or smoke passing through the dust passage route, because light from light-emitting unit 15 will pass through the dust passage route and reach optical isolation region 18, the amount of light received at light-receiving unit 16 will be extremely small. Furthermore, in the event that there is dust and/or smoke passing through the dust passage route, because a portion of the light from light-emitting unit 15 will be reflected by the dust and/or smoke in the dust passage route and will be incident on light-receiving unit 16, the amount of light received at light-receiving unit 16 will increase. Accordingly, presence and/or absence of dust and/or smoke passing through the dust passage route may be detected based on variation in received-light output at light-receiving element 16a of light-receiving unit 16; and/or concentration of dust and/or smoke passing through the dust passage route may be detected based on the received-light output level at light-receiving element 16a.

Figure 2:
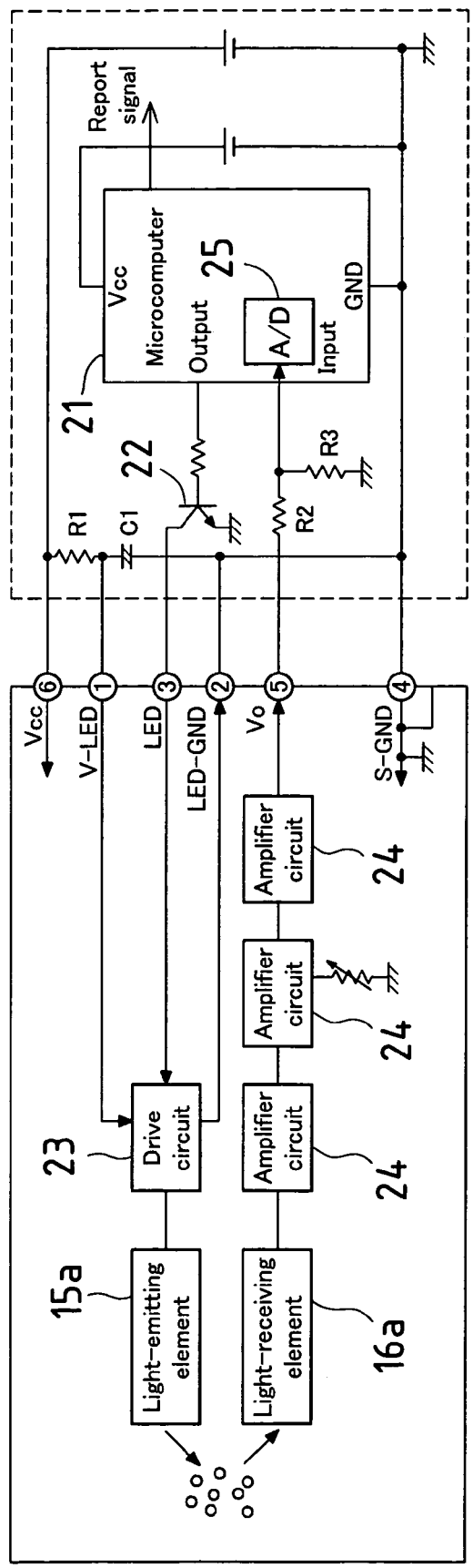
FIG. 2 is a block diagram showing constitution of an optoelectronic dust sensor in accordance with the present embodiment.
Figure 3:
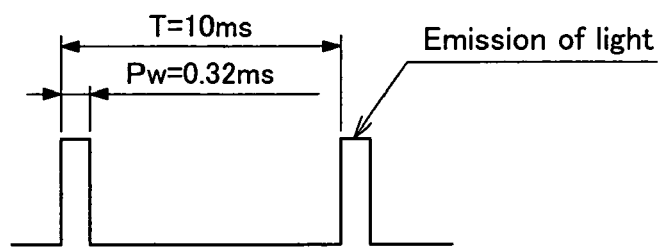
FIG. 3 is a diagram showing pulsewidth and period of an optical pulse from a light-emitting element at the sensor of FIG. 2.

FIG. 2 is a block diagram showing constitution of optoelectronic dust sensor 11 in accordance with the present embodiment. At this optoelectronic dust sensor 11, microcomputer 21 controls driving of light-emitting element 15a by way of transistor 22 and drive circuit 23 so as to cause light-emitting element 15a to cyclically emit light in pulsed fashion as indicated at FIG. 3. Optical pulses emitted toward the dust passage route by light-emitting element 15a have pulsewidth Pw and are emitted with period T. Light-receiving element 16a does not receive light when there is no dust or smoke in the dust passage route; but when there is dust and/or smoke in the dust passage route, light-receiving element 16a receives light reflected by this dust and/or smoke and outputs signal(s) corresponding to received-light level(s). Because the signal from light-receiving element 16a is weak, it is amplified by three-stage amplifier 24 before being input at A/D converter 25 of microcomputer 21.

Note that there is no objection to provision of peak hold circuit(s) to hold amplified output(s) at location(s) downstream from any of the amplifier 24 stages.

At microcomputer 21, A/D converter 25 carries out A/D conversion on signal level(s) (received-light level(s)) at light-receiving element 16a, and compares such signal level(s) with threshold value(s) previously stored in EEPROM (not shown). If such signal level is less than the threshold value, then it is determined that there is no dust or smoke in the dust passage route. But if such signal level is greater than or equal to the threshold value, then it is determined that there is dust and/or smoke in the dust passage route. Moreover, in the event that it is determined that there is dust and/or smoke in the dust passage route, a detection signal is output indicating that dust and/or smoke is present. Alternatively or in addition thereto, concentration(s) of dust and/or smoke might be determined in correspondence to signal level(s) at light-receiving element 16a, and detection signal(s) might be output indicating such concentration(s) of dust and/or smoke.

Figure 4:
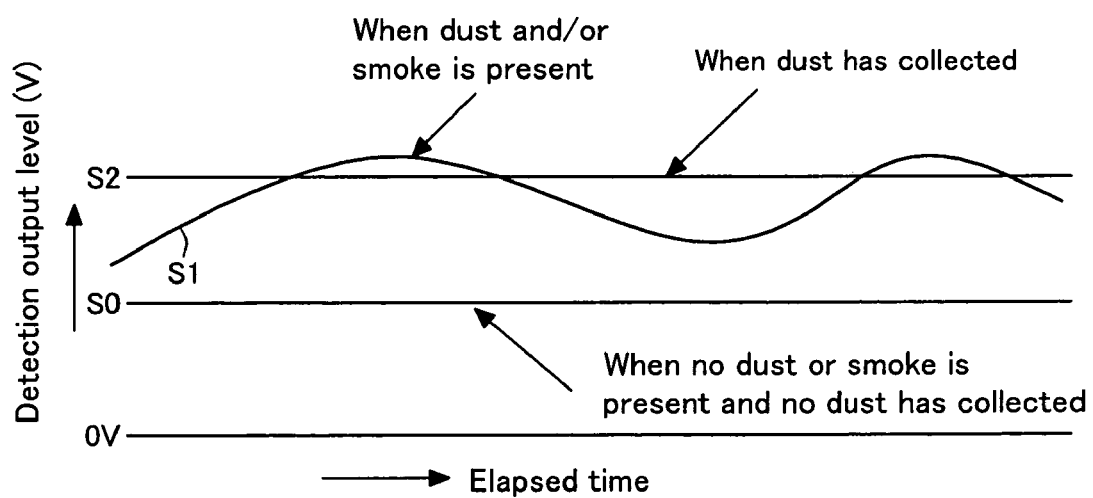
FIG. 4 is a graph showing light-receiving element signal level at the sensor of FIG. 2.

It so happens even when there is no dust or smoke in the dust passage route of optoelectronic dust sensor 11 that light from light-emitting unit 15 will nonetheless be reflected in diffuse fashion within main body housing 12 and a small amount of light will be received at light-receiving unit 16, as a result of which the signal level (received-light level) at light-receiving element 16a when no dust is detected would be a constant value S0 as shown in FIG. 4.

Furthermore, the signal level at light-receiving element 16a might vary as indicated by curve S1 in correspondence to concentration of dust and/or smoke passing through the dust passage route.

In addition, value S0 of the signal level when no dust is detected represents the situation when absolutely no dust or smoke has accumulated within main body housing 12, the level of the signal when no dust is detected increasing as the amount of deposits collected within main body housing 12 increases. For example, the signal level when no dust is detected might increase to on the order of value S2. At such time, because higher level S2 is added to curve S1 corresponding to dust and/or smoke concentration, causing saturation output voltage to be reached, it will no longer be possible to determine presence, absence, and/or concentration of dust and/or smoke based on signal level.

Microcomputer 21 therefore keeps track of the time during which the signal level from light-receiving element 16a continues to be maintained in the vicinity of value S2, and in the event that such time reaches, e.g., several tens of minutes; i.e., in the event that a high signal level is maintained for a long period of time, this is interpreted as meaning that a large amount of deposits have collected within main body housing 12, and a report signal indicating such fact might be output, a buzzer might be sounded, and/or an LED might be made to flash. This makes it possible to report that a large amount of deposits have collected within main body housing 12.

And in the event that the signal level from light-receiving element 16a is less than approximately value S2 for several tens of minutes, this is interpreted as meaning that the signal level from light-receiving element 16a is varying in correspondence to change in dust and/or smoke concentration.

Here, because it will be impossible to carry out determination as to presence, absence, and/or concentration of dust and/or smoke when it has been reported that a large amount of deposits have collected within main body housing 12, the deposits must be removed from main body housing 12.

Opening 13a at main body housing 12 is sufficiently larger than passage hole 14a. This being the case, it will be possible using, for example, a cotton-tipped swab or the like to easily scrape out and remove deposits within main body housing 12 by way of opening 13a. Furthermore, because opening 13a is large enough to permit access to portions corresponding to lens 15b of light-emitting unit 15 and lens 16b of light-receiving unit 16, it is possible to easily wipe off and remove deposits accumulating on respective lenses 16b, 16b.

Moreover, because wide opening 13a is provided at the side from which dust and/or smoke is discharged, discharge of dust and/or smoke is facilitated. Furthermore, there is also the advantage that this reduces the tendency for dust and/or smoke to accumulate within main body housing 12.

Furthermore, by arranging main body housing 12 of optoelectronic dust sensor 11 such that small passage hole 14a is directed toward the bright side thereof and such that large opening 13a is directed toward the dark side thereof, it is possible to reduce the level of exterior light incident at main body housing 12 by way of small passage hole 14a, reducing likelihood of occurrence of mistaken detection of dust and/or smoke at light-receiving unit 16.

For example, where optoelectronic dust sensor 11 is disposed near an air inlet of an air filter, air scrubber, air cooler, and/or other such air conditioning equipment, main body housing 12 might be arranged such that opening 13a of main body housing 12 is directed toward the air inlet side (i.e., inside) of the air conditioning equipment, and such that passage hole 14a of main body housing 12 is directed toward the outside of the air conditioning equipment. This being the case, dust and/or smoke will be carried together with air from passage hole 14a of main body housing 12 and out through opening 13a thereof, reducing the tendency for dust and/or smoke to collect within main body housing 12. Furthermore, small passage hole 14a being directed toward the bright outside of the air conditioning equipment, and large opening 13a being directed toward the dark air-inlet side (i.e., inside) of the air conditioning equipment, the level of exterior light incident at main body housing 12 by way of small passage hole 14a is reduced, decreasing likelihood of occurrence of mistaken detection of dust and/or smoke at light-receiving unit 16.

Figure 5:
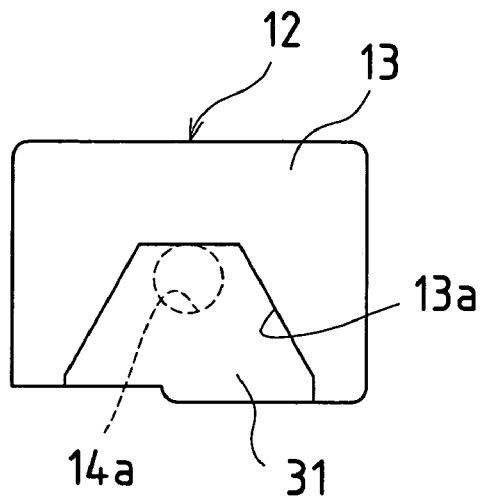
FIG. 5 is a drawing showing a variation on the sensor of FIG. 1.
Figure 6:
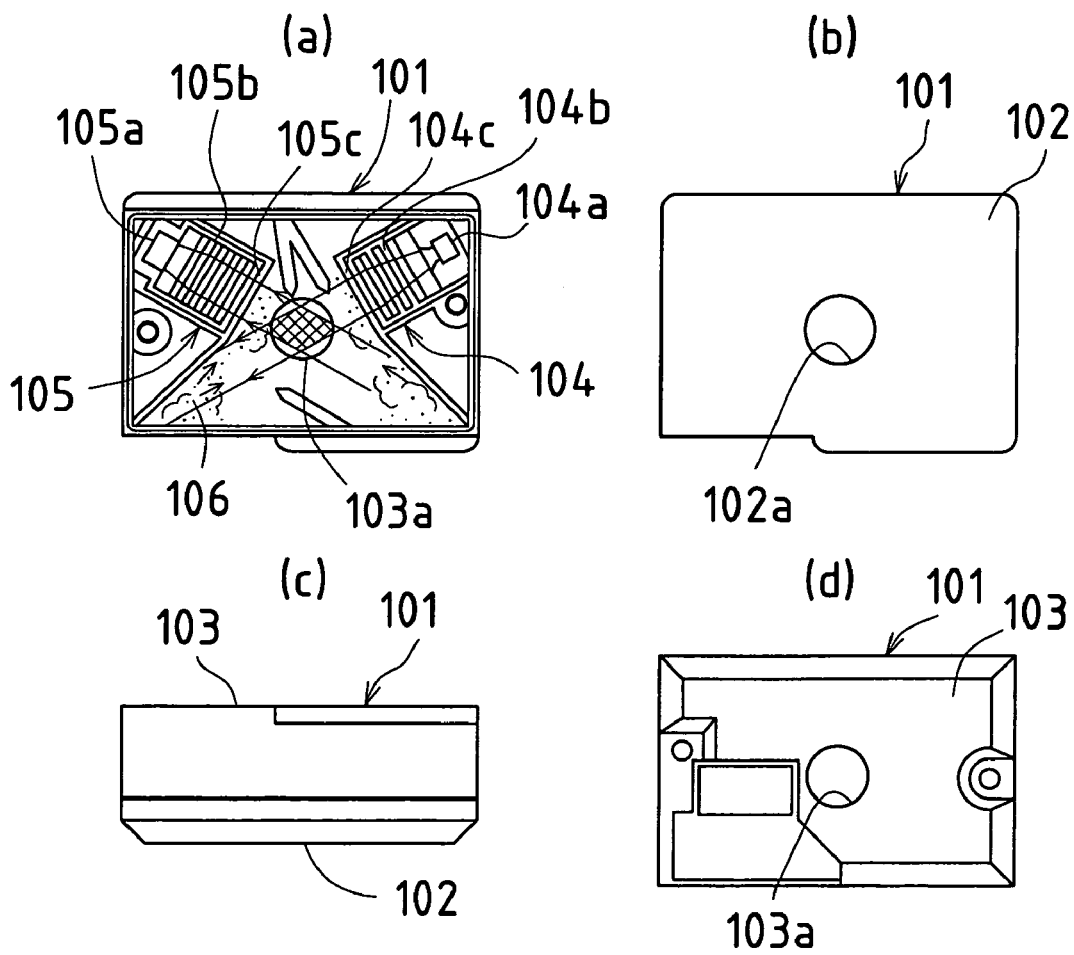
FIG. 6(a), FIG. 6(b), FIG. 6(c), and FIG. 6(d) are a sectional view, front view, bottom view, and rear view showing a conventional optoelectronic dust sensor.

Moreover, a great many variations of the present invention being possible, the invention is not to be limited by the foregoing embodiment(s). For example, as shown in FIG. 5, there is no objection to provision of slidable cover 31 removably installed at opening 13a of main body housing 12. Where this is present, opening 13a may be uncovered as appropriate by appropriately sliding cover 31. Furthermore, cover 31 might be completely detached from opening 13a when removing dust and/or smoke from main body housing 12.

Furthermore, there is no objection to appropriate modification of shape(s), location(s), size(s), and/or the like of opening(s) 13a and/or passage hole(s) 14a at main body housing(s) 12.

As described above, in embodiment(s) of the present invention, passage hole(s) and opening(s) may be formed on main body housing(s) of optoelectronic dust sensor(s), dust passage route(s) may be provided between passage hole(s) and opening(s), and opening(s) may be larger than passage hole(s). Wide opening(s) provided at side(s) from which dust is discharged may facilitate discharge of dust. Furthermore, dust may be less likely to collect within main body housing(s). Furthermore, it may be the case that deposits within main body housing(s) can be easily removed by way of large opening(s). In addition, by arranging main body housing(s) of optoelectronic dust sensor(s) such that small passage hole(s) is/are directed toward bright side(s) and large opening(s) is/are directed toward dark side(s), it is possible to reduce level(s) of exterior light incident at main body housing(s) by way of small passage hole(s), reducing likelihood of occurrence of mistaken detection of dust at light-receiving unit(s).

Note that the optoelectronic dust sensor of the present invention is effective not only with respect to detection of dust but also with respect to detection of presence, absence, and/or concentration of smoke and/or the like.

The present invention may be embodied in a wide variety of forms other than those presented herein without departing from the spirit or essential characteristics thereof. The foregoing embodiments and working examples, therefore, are in all respects merely illustrative and are not to be construed in limiting fashion. The scope of the present invention being as indicated by the claims, it is not to be constrained in any way whatsoever by the body of the specification. All modifications and changes within the range of equivalents of the claims are moreover within the scope of the present invention.

What is claimed is:

1. An optoelectronic dust sensor comprising:
   one or more light-emitting units irradiating one or more dust passage routes with light;
   one or more light-receiving units receiving light reflected from dust passing through at least one of the dust passage route or routes;
   one or more main body housings at least partially enclosing the optoelectronic dust sensor;
   one or more passage holes, provided at at least one of the main body housing or housings, for permitting introduction of dust from the exterior to at least one of the dust passage route or routes;
   one or more openings, provided at at least one of the main body housing or housings, for permitting discharge of dust from at least one of the dust passage route or routes to the exterior;
   wherein presence, absence, and/or concentration of dust is detected based on received-light output from at least one of the light-receiving unit or units;
   at least one of the opening or openings is larger than at least one of the passage hole or holes;
   at least one detection report means for detecting and reporting at least one large amount(s) of dust accumulated at the interior of at least one of the main body housing or housings of the optoelectronic dust sensor; and
   wherein said detection report means keeps track of a time during which a signal level from the light-receiving unit is maintained at or above a predetermined level, and when the time exceeds a predetermined threshold said detection report means reports that a large amount of deposit(s) may have collected within the main body housing(s).

2. An optoelectronic dust sensor according to claim 1 wherein: at least one of the opening or openings is provided with at least one removably installed cover.

3. Air conditioning equipment wherein, when one or more optoelectronic dust sensors according to claim 2 is or are disposed near one or more air inlets of the air conditioning equipment, at least one of the main body housing or housings is or are arranged near at least one of the air inlet or inlets of the air conditioning equipment, such that at least one of the opening or openings of at least one of the optoelectronic sensor or sensors is directed toward an air inlet side or an inside of the air conditioning equipment and such that at least one of the passage hole or holes of at least one of the optoelectronic sensor or sensors is directed toward an outside of the air conditioning equipment.

4. An optoelectronic dust sensor according to claim 2 wherein at least one of the opening or openings is provided with at least one sliding cover.

5. Air conditioning equipment wherein, when one or more optoelectronic dust sensors according to claim 4 is or are disposed near one or more air inlets of the air conditioning equipment, at least one of the main body housing or housings is or are arranged near at least one of the air inlet or inlets of the air conditioning equipment, such that at least one of the opening or openings of at least one of the optoelectronic sensor or sensors is directed toward an air inlet side or an inside of the air conditioning equipment, and such that at least one of the passage hole or holes of at least one of the optoelectronic sensor or sensors is directed toward an outside of the air conditioning equipment.

6. Air conditioning equipment wherein, when one or more optoelectronic dust sensors according to claim 1 is or are disposed near one or more air inlets of the air conditioning equipment, at least one of the main body housing or housings is or are arranged near at least one of the air inlet or inlets of the air conditioning equipment, such that at least one of the opening or openings of at least one of the optoelectronic sensor or sensors is directed toward an air inlet side or an inside of the air conditioning equipment and such that at least one of the passage hole or holes of at least one of the optoelectronic sensor or sensors is directed toward an outside of the air conditioning equipment.

* * * * *